US009709960B2

(12) United States Patent
Cho et al.

(10) Patent No.: US 9,709,960 B2
(45) Date of Patent: Jul. 18, 2017

(54) WATCH-TYPE MOBILE TERMINAL AND METHOD OF CONTROLLING THE SAME

(71) Applicant: LG ELECTRONICS INC., Seoul (KR)

(72) Inventors: Jaesung Cho, Seoul (KR); Gimun Kim, Seoul (KR); Dongjin Kim, Seoul (KR); Ohboum Kwon, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 92 days.

(21) Appl. No.: 14/666,127

(22) Filed: Mar. 23, 2015

(65) Prior Publication Data

US 2016/0187857 A1 Jun. 30, 2016

(30) Foreign Application Priority Data

Dec. 29, 2014 (KR) ........................ 10-2014-0192326

(51) Int. Cl.

| | |
|---|---|
| ***H01Q 1/24*** | (2006.01) |
| ***A61B 5/01*** | (2006.01) |
| ***G04R 20/00*** | (2013.01) |
| ***G04R 60/04*** | (2013.01) |
| ***H01Q 1/27*** | (2006.01) |
| ***H01Q 1/48*** | (2006.01) |
| ***G04R 20/26*** | (2013.01) |

(52) U.S. Cl.

CPC ............. *G04R 20/00* (2013.01); *G04R 20/26* (2013.01); *G04R 60/04* (2013.01); *H01Q 1/273* (2013.01); *H01Q 1/48* (2013.01)

(58) Field of Classification Search

CPC combination set(s) only.
See application file for complete search history.

(56) References Cited

U.S. PATENT DOCUMENTS

| | | | | |
|---|---|---|---|---|
| 5,007,105 A | | 4/1991 | Kudoh et al. | |
| 2002/0151775 A1 | * | 10/2002 | Kondo | A61B 5/02438 600/344 |
| 2003/0119469 A1 | * | 6/2003 | Karr | H01Q 1/273 455/307 |
| 2005/0084075 A1 | * | 4/2005 | Kotzin | H04M 1/72569 379/38 |
| 2007/0238418 A1 | * | 10/2007 | Mizusawa | H04W 16/14 455/69 |

(Continued)

OTHER PUBLICATIONS

European Patent Office Application Serial No. 15164974.6, Search Report dated Jun. 6, 2016, 6 pages.

*Primary Examiner* — Brian Zimmerman
*Assistant Examiner* — Cal Eustaquio
(74) *Attorney, Agent, or Firm* — Lee Hong Degerman Kang & Waimey

(57) ABSTRACT

Provided is a watch-type terminal including: a main body that includes an antenna module which transmits and receives a wireless signal in a predetermined frequency band; a band that extends from the main body and that is formed in such a manner that the main body is removably worn on a wrist; a ground portion that includes first and second metal members that extend to have different lengths; a sensing unit that detects whether or not the main body is worn on the wrist; and a controller that grounds the antenna module to at least one of the first and second metal members, based on whether or not the main body is worn on the wrist.

15 Claims, 12 Drawing Sheets

(56) References Cited

U.S. PATENT DOCUMENTS

| | | | | |
|---|---|---|---|---|
| 2009/0053997 | A1* | 2/2009 | Jobling | G06F 3/01 455/41.2 |
| 2010/0231471 | A1* | 9/2010 | Haglund | H01Q 1/273 343/729 |
| 2011/0012796 | A1* | 1/2011 | Kim | G04R 60/12 343/702 |
| 2013/0072765 | A1 | 3/2013 | Kahn et al. | |

* cited by examiner

WATCH-TYPE MOBILE TERMINAL AND METHOD OF CONTROLLING THE SAME

CROSS-REFERENCE TO RELATED APPLICATION

Pursuant to 35 U.S.C. §119(a), this application claims the benefit of earlier filing date and right of priority to Korean Application No. 10-2014-0192326, filed on Dec. 29, 2014, the contents of which are incorporated by reference herein in its entirety.

BACKGROUND OF THE DISCLOSURE

1. Field of the Disclosure

The present disclosure relates to a watch-type mobile terminal that is configured to be capable of being worn on a wrist.

2. Background of the Disclosure

A terminal is broadly categorized by mobility into a mobile terminal and a stationary terminal. The mobile terminal is further categorized by portability into a handheld terminal and a vehicle-mounted terminal.

In response to an increasing demand for diversified functions, the terminal has been realized in the form of a multimedia player with multiple functions such as shooting a photographic object as a still image or moving images, reproducing digital audio and video compression files, playing a game, receiving a broadcast or the like. Furthermore, structural and software modifications to the mobile terminal are considered for supporting and improving functions of the mobile terminal.

Recent watch-type terminals equipped with various functions include a wireless signal transmission and reception module for performing wireless communication in various frequency bands. However, in a case where only a size-limited circuit board and a frame that makes up the external appearance of the watch-type terminal are configured as a ground portion of the wireless signal transmission and reception module, it is difficult to secure communication quality in a low band.

In addition, in a case where the watch-type terminal is worn on a user's wrist or is removed from the user's wrist, there occurs a problem in that constant-quality wireless signal transmission and reception cannot be performed due to an influence of a user's body.

SUMMARY OF THE DISCLOSURE

Therefore, an aspect of the detailed description is to provide (공런)

To achieve these and other advantages and in accordance with the purpose of this specification, as embodied and broadly described herein, there is provided a watch-type terminal including: a main body that includes an antenna module which transmits and receives a wireless signal in a predetermined frequency band; a band that extends from the main body and that is formed in such a manner that the main body is removably worn on a wrist; a ground portion that includes first and second metal members that extend to have different lengths; a sensing unit that detects whether or not the main body is worn on the wrist; and a controller that grounds the antenna module at least one of the first and second metal members, based on whether or not the main body is worn on the wrist.

According to one embodiment of the present invention, the sensing unit is configured as a sensing module that collects biological information on a user, a sensing module that measures a value of capacitance that varies depending on whether or not the main body is worn on the user's wrist, or a communication measurement sensor that measures wireless communication quality of the antenna module. Thus, there is no need for the user to input an additional control command for controlling grounding.

In addition, because the antenna module can be grounded to the first and second metal members that have different lengths based on the capacitance that varies depending on whether or not the main body comes into contact with a user's body, the grounded state of the antenna module that varies depending on whether or not the main body is worn on the user's wrist is provided. Thus, wireless communication performance of the antenna module can be improved in both a worn state of the main body and a non-worn state of the main body.

According to the present invention, in a case where the main body into which the antenna is built approaches the user's body, the antenna is selectively grounded to the metal member that is shorter in length, thereby minimizing an influence that a change in the dielective constant due to an influence of the body takes on the wireless communication.

In addition, it is detected whether or not the watch-type terminal is worn on the user's body, and the grounding of the antenna is controlled depending on whether or not the watch-type terminal is worn on the user's body. Thus, there is no need for the user to perform a separate control step.

Further scope of applicability of the present application will become more apparent from the detailed description given hereinafter. However, it should be understood that the detailed description and specific examples, while indicating preferred embodiments of the disclosure, are given by way of illustration only, since various changes and modifications within the spirit and scope of the disclosure will become apparent to those skilled in the art from the detailed description.

BRIEF DESCRIPTION OF THE DRAWINGS

The accompanying drawings, which are included to provide a further understanding of the disclosure and are incorporated in and constitute a part of this specification, illustrate exemplary embodiments and together with the description serve to explain the principles of the disclosure.

In the drawings.

DETAILED DESCRIPTION OF THE DISCLOSURE

Figure 1:
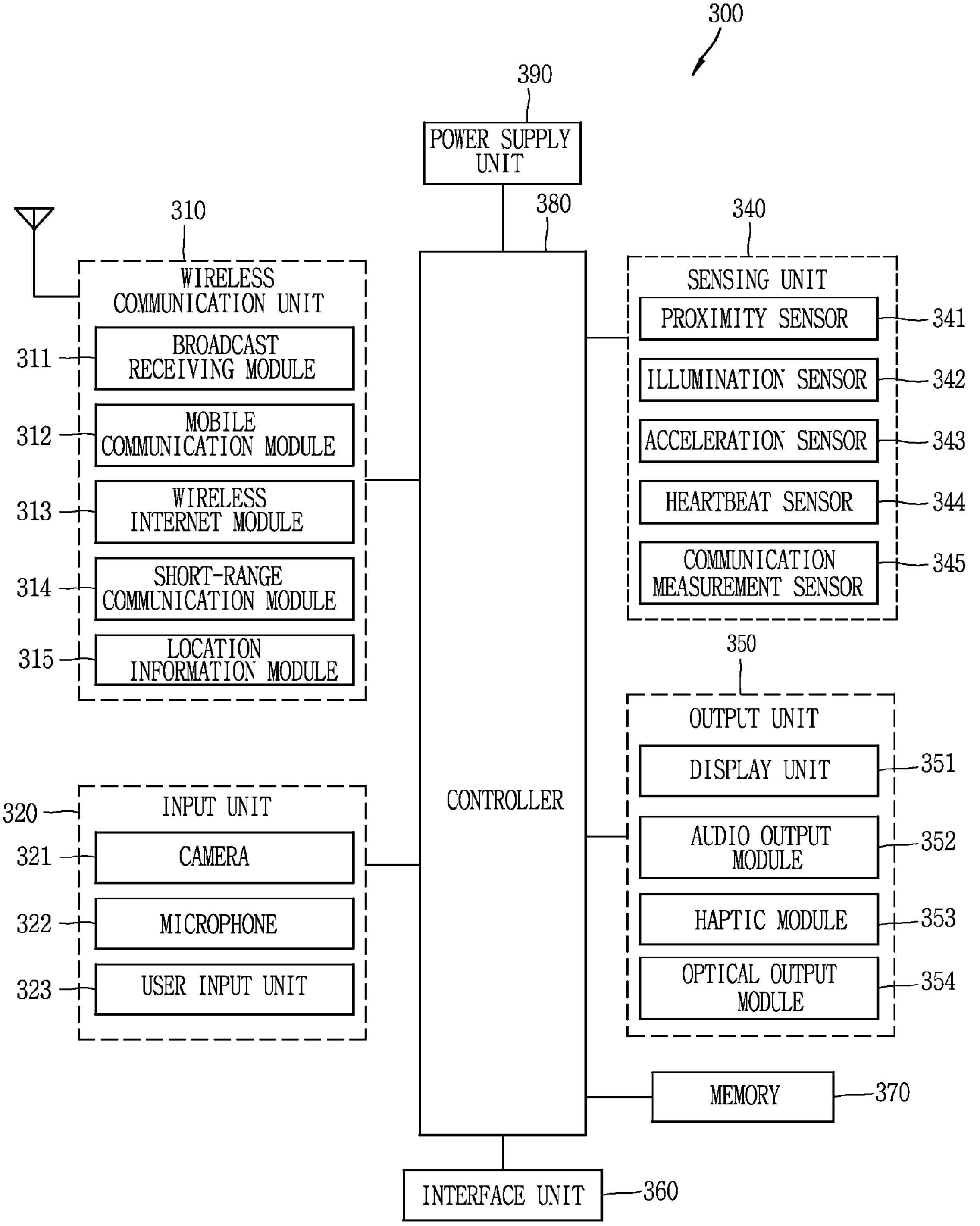
FIG. 1 is a block diagram for describing a configuration of a watch-type terminal according to the present invention.

Description will now be given in detail according to exemplary embodiments disclosed herein, with reference to the accompanying drawings. For the sake of brief description with reference to the drawings, the same or equivalent components may be provided with the same or similar reference numbers, and description thereof will not be repeated. In general, a suffix such as "module" and "unit" may be used to refer to elements or components. Use of such a suffix herein is merely intended to facilitate description of the specification, and the suffix itself is not intended to give any special meaning or function. In the present disclosure, that which is well-known to one of ordinary skill in the relevant art has generally been omitted for the sake of brevity. The accompanying drawings are used to help easily understand various technical features and it should be understood that the embodiments presented herein are not limited by the accompanying drawings. As such, the present disclosure should be construed to extend to any alterations, equivalents and substitutes in addition to those which are particularly set out in the accompanying drawings.

It will be understood that although the terms first, second, etc. may be used herein to describe various elements, these elements should not be limited by these terms. These terms are generally only used to distinguish one element from another.

It will be understood that when an element is referred to as being "connected with" another element, the element can be connected with the other element or intervening elements may also be present. In contrast, when an element is referred to as being "directly connected with" another element, there are no intervening elements present.

A singular representation may include a plural representation unless it represents a definitely different meaning from the context.

Terms such as "include" or "has" are used herein and should be understood that they are intended to indicate an existence of several components, functions or steps, disclosed in the specification, and it is also understood that greater or fewer components, functions, or steps may likewise be utilized.

Mobile terminals presented herein may be implemented using a variety of different types of terminals. Examples of such terminals include cellular phones, smart phones, user equipment, laptop computers, digital broadcast terminals, personal digital assistants (PDAs), portable multimedia players (PMPs), navigators, portable computers (PCs), slate PCs, tablet PCs, ultra books, wearable devices (for example, smart watches, smart glasses, head mounted displays (HMDs)), and the like.

By way of non-limiting example only, further description will be made with reference to particular types of mobile terminals. However, such teachings apply equally to other types of terminals, such as those types noted above. In addition, these teachings may also be applied to stationary terminals such as digital TV, desktop computers, digital signage and the like.

FIG. 1 is a block diagram of a watch-type mobile terminal in accordance with the present disclosure.

The mobile terminal 300 is shown having components such as a wireless communication unit 310, an input unit 320, a sensing unit 340, an output unit 350, an interface unit 360, a memory 370, a controller 380, and a power supply unit 390. It is understood that implementing all of the illustrated components is not a requirement, and that greater or fewer components may alternatively be implemented.

Referring now to FIG. 1, the mobile terminal 100 is shown having wireless communication unit 310 configured with several commonly implemented components. For instance, the wireless communication unit 310 typically includes one or more components which permit wireless communication between the mobile terminal 300 and a wireless communication system or network within which the mobile terminal is located.

The wireless communication unit 310 typically includes one or more modules which permit communications such as wireless communications between the mobile terminal 300 and a wireless communication system, communications between the mobile terminal 300 and another mobile terminal, communications between the mobile terminal 300 and an external server. Further, the wireless communication unit 310 typically includes one or more modules which connect the mobile terminal 300 to one or more networks. To facilitate such communications, the wireless communication unit 310 includes one or more of a broadcast receiving module 311, a mobile communication module 312, a wireless Internet module 313, a short-range communication module 314, and a location information module 315.

The input unit 320 includes a camera 321 for obtaining images or video, a microphone 322, which is one type of audio input device for inputting an audio signal, and a user input unit 323 (for example, a touch key, a push key, a mechanical key, a soft key, and the like) for allowing a user to input information. Data (for example, audio, video, image, and the like) is obtained by the input unit 320 and may be analyzed and processed by controller 380 according to device parameters, user commands, and combinations thereof.

The sensing unit 340 is typically implemented using one or more sensors configured to sense internal information of the mobile terminal, the surrounding environment of the mobile terminal, user information, and the like. For example, in FIG. 1, the sensing unit 340 is shown having a proximity sensor 341 and an illumination sensor 342.

If desired, the sensing unit 340 may alternatively or additionally include other types of sensors or devices, such as a touch sensor, an acceleration sensor, a magnetic sensor, a G-sensor, a gyroscope sensor, a motion sensor, an RGB sensor, an infrared (IR) sensor, a finger scan sensor, a ultrasonic sensor, an optical sensor (for example, camera 321), a microphone 322, a battery gauge, an environment sensor (for example, a barometer, a hygrometer, a thermometer, a radiation detection sensor, a thermal sensor, and a gas sensor, among others), and a chemical sensor (for example, an electronic nose, a health care sensor, a biometric sensor, and the like), to name a few. The mobile terminal 300 may be configured to utilize information obtained from sensing unit 340, and in particular, information obtained from one or more sensors of the sensing unit 340, and combinations thereof.

The output unit 350 is typically configured to output various types of information, such as audio, video, tactile output, and the like. The output unit 350 is shown having a display unit 351, an audio output module 352, a haptic module 353, and an optical output module 354.

The display unit 351 may have an inter-layered structure or an integrated structure with a touch sensor in order to facilitate a touch screen. The touch screen may provide an output interface between the mobile terminal 300 and a user, as well as function as the user input unit 323 which provides an input interface between the mobile terminal 300 and the user.

The interface unit 360 serves as an interface with various types of external devices that can be coupled to the mobile terminal 300. The interface unit 360, for example, may include any of wired or wireless ports, external power supply ports, wired or wireless data ports, memory card ports, ports for connecting a device having an identification module, audio input/output (I/O) ports, video I/O ports, earphone ports, and the like. In some cases, the mobile terminal 100 may perform assorted control functions associated with a connected external device, in response to the external device being connected to the interface unit 360.

The memory 370 is typically implemented to store data to support various functions or features of the mobile terminal 300. For instance, the memory 370 may be configured to store application programs executed in the mobile terminal 300, data or instructions for operations of the mobile terminal 300, and the like. Some of these application programs may be downloaded from an external server via wireless communication. Other application programs may be installed within the mobile terminal 300 at time of manufacturing or shipping, which is typically the case for basic functions of the mobile terminal 300 (for example, receiving a call, placing a call, receiving a message, sending a message, and the like). It is common for application programs to be stored in the memory 370, installed in the mobile terminal 300, and executed by the controller 380 to perform an operation (or function) for the mobile terminal 300.

The controller 380 typically functions to control overall operation of the mobile terminal 300, in addition to the operations associated with the application programs. The controller 380 may provide or process information or functions appropriate for a user by processing signals, data, information and the like, which are input or output by the various components depicted in FIG. 1, or activating application programs stored in the memory 370. As one example, the controller 380 controls some or all of the components illustrated in FIG. 1 according to the execution of an application program that have been stored in the memory 370.

The power supply unit 390 can be configured to receive external power or provide internal power in order to supply appropriate power required for operating elements and components included in the mobile terminal 300. The power supply unit 390 may include a battery, and the battery may be configured to be embedded in the terminal body, or configured to be detachable from the terminal body.

At least some of the above components may operate in a cooperating manner, so as to implement an operation or a control method of a glass type terminal according to various embodiments to be explained later. The operation or the control method of the glass type terminal may be implemented on the glass type terminal by driving at least one application program stored in the memory 370.

Referring still to FIG. 1A, various components depicted in this figure will now be described in more detail.

Regarding the wireless communication unit 310, the broadcast receiving module 311 is typically configured to receive a broadcast signal and/or broadcast associated information from an external broadcast managing entity via a broadcast channel. The broadcast channel may include a satellite channel, a terrestrial channel, or both. In some embodiments, two or more broadcast receiving modules 311 may be utilized to facilitate simultaneously receiving of two or more broadcast channels, or to support switching among broadcast channels.

The mobile communication module 312 can transmit and/or receive wireless signals to and from one or more network entities. Typical examples of a network entity include a base station, an external mobile terminal, a server, and the like. Such network entities form part of a mobile communication network, which is constructed according to technical standards or communication methods for mobile communications (for example, Global System for Mobile Communication (GSM), Code Division Multi Access (CDMA), CDMA2000(Code Division Multi Access 2000), EV-DO(Enhanced Voice-Data Optimized or Enhanced Voice-Data Only), Wideband CDMA (WCDMA), High Speed Downlink Packet access (HSDPA), HSUPA(High Speed Uplink Packet Access), Long Term Evolution (LTE), LTE-A(Long Term Evolution-Advanced), and the like).

Examples of wireless signals transmitted and/or received via the mobile communication module 312 include audio call signals, video (telephony) call signals, or various formats of data to support communication of text and multimedia messages.

The wireless Internet module 313 is configured to facilitate wireless Internet access. This module may be internally or externally coupled to the mobile terminal 300. The wireless Internet module 313 may transmit and/or receive wireless signals via communication networks according to wireless Internet technologies.

Examples of such wireless Internet access include Wireless LAN (WLAN), Wireless Fidelity (Wi-Fi), Wi-Fi Direct, Digital Living Network Alliance (DLNA), Wireless Broadband (WiBro), Worldwide Interoperability for Microwave Access (WiMAX), High Speed Downlink Packet Access (HSDPA), HSUPA(High Speed Uplink Packet Access), Long Term Evolution (LTE), LTE-A(Long Term Evolution-Advanced), and the like. The wireless Internet module 113 may transmit/receive data according to one or more of such wireless Internet technologies, and other Internet technologies as well.

In some embodiments, when the wireless Internet access is implemented according to, for example, WiBro, HSDPA, HSUPA, GSM, CDMA, WCDMA, LTE, LTE-A and the like, as part of a mobile communication network, the wireless Internet module 113 performs such wireless Internet access. As such, the Internet module 113 may cooperate with, or function as, the mobile communication module 112.

The short-range communication module 314 is configured to facilitate short-range communications. Suitable technologies for implementing such short-range communications include BLUETOOTH™, Radio Frequency IDentification (RFID), Infrared Data Association (IrDA), Ultra-WideBand (UWB), ZigBee, Near Field Communication (NFC), Wireless-Fidelity (Wi-Fi), Wi-Fi Direct, Wireless USB(Wireless Universal Serial Bus), and the like. The short-range communication module 314 in general supports wireless communications between the mobile terminal 300 and a wireless communication system, communications between the mobile terminal 300 and another mobile terminal 300, or communications between the mobile terminal and a network where another mobile terminal 300 (or an external server) is located, via wireless area networks. One example of the wireless area networks is a wireless personal area networks.

In some embodiments, another mobile terminal (which may be configured similarly to mobile terminal 300) may be a wearable device, for example, a smart watch, a smart glass or a head mounted display (HMD), which is able to exchange data with the mobile terminal 300 (or otherwise cooperate with the mobile terminal 300). The short-range communication module 314 may sense or recognize the wearable device, and permit communication between the wearable device and the mobile terminal 300. In addition, when the sensed wearable device is a device which is authenticated to communicate with the mobile terminal 300, the controller 380, for example, may cause transmission of data processed in the mobile terminal 300 to the wearable device via the short-range communication module 314. Hence, a user of the wearable device may use the data processed in the mobile terminal 300 on the wearable device. For example, when a call is received in the mobile terminal 300, the user may answer the call using the wearable device. Also, when a message is received in the mobile terminal 300, the user can check the received message using the wearable device.

The location information module 315 is generally configured to detect, calculate, derive or otherwise identify a position of the mobile terminal. As an example, the location information module 315 includes a Global Position System (GPS) module, a Wi-Fi module, or both. If desired, the location information module 315 may alternatively or additionally function with any of the other modules of the wireless communication unit 310 to obtain data related to the position of the mobile terminal.

As one example, when the mobile terminal uses a GPS module, a position of the mobile terminal may be acquired using a signal sent from a GPS satellite. As another example, when the mobile terminal uses the Wi-Fi module, a position of the mobile terminal can be acquired based on information related to a wireless access point (AP) which transmits or receives a wireless signal to or from the Wi-Fi module.

The input unit 320 may be configured to permit various types of input to the mobile terminal 320. Examples of such input include audio, image, video, data, and user input. Image and video input is often obtained using one or more cameras 321. Such cameras 321 may process image frames of still pictures or video obtained by image sensors in a video or image capture mode. The processed image frames can be displayed on the display unit 351 or stored in memory 370. In some cases, the cameras 321 may be arranged in a matrix configuration to permit a plurality of images having various angles or focal points to be input to the mobile terminal 300. As another example, the cameras 321 may be located in a stereoscopic arrangement to acquire left and right images for implementing a stereoscopic image.

The microphone 322 is generally implemented to permit audio input to the mobile terminal 300. The audio input can be processed in various manners according to a function being executed in the mobile terminal 300. If desired, the microphone 322 may include assorted noise removing algorithms to remove unwanted noise generated in the course of receiving the external audio.

The user input unit 323 is a component that permits input by a user. Such user input may enable the controller 380 to control operation of the mobile terminal 300. The user input unit 323 may include one or more of a mechanical input element (for example, a key, a button located on a front and/or rear surface or a side surface of the mobile terminal 300, a dome switch, a jog wheel, a jog switch, and the like), or a touch-sensitive input, among others. As one example, the touch-sensitive input may be a virtual key or a soft key, which is displayed on a touch screen through software processing, or a touch key which is located on the mobile terminal at a location that is other than the touch screen. On the other hand, the virtual key or the visual key may be displayed on the touch screen in various shapes, for example, graphic, text, icon, video, or a combination thereof.

The sensing unit 340 is generally configured to sense one or more of internal information of the mobile terminal, surrounding environment information of the mobile terminal, user information, or the like. The controller 380 generally cooperates with the sending unit 340 to control operation of the mobile terminal 300 or execute data processing, a function or an operation associated with an application program installed in the mobile terminal based on the sensing provided by the sensing unit 340. The sensing unit 340 may be implemented using any of a variety of sensors, some of which will now be described in more detail.

The proximity sensor 341 may include a sensor to sense presence or absence of an object approaching a surface, or an object located near a surface, by using an electromagnetic field, infrared rays, or the like without a mechanical contact. The proximity sensor 341 may be arranged at an inner region of the mobile terminal covered by the touch screen, or near the touch screen.

The proximity sensor 341, for example, may include any of a transmissive type photoelectric sensor, a direct reflective type photoelectric sensor, a mirror reflective type photoelectric sensor, a high-frequency oscillation proximity sensor, a capacitance type proximity sensor, a magnetic type proximity sensor, an infrared rays proximity sensor, and the like. When the touch screen is implemented as a capacitance type, the proximity sensor 341 can sense proximity of a pointer relative to the touch screen by changes of an electromagnetic field, which is responsive to an approach of an object with conductivity. In this case, the touch screen (touch sensor) may also be categorized as a proximity sensor.

The term "proximity touch" will often be referred to herein to denote the scenario in which a pointer is positioned to be proximate to the touch screen without contacting the touch screen. The term "contact touch" will often be referred to herein to denote the scenario in which a pointer makes physical contact with the touch screen. For the position corresponding to the proximity touch of the pointer relative to the touch screen, such position will correspond to a position where the pointer is perpendicular to the touch screen. The proximity sensor 341 may sense proximity touch, and proximity touch patterns (for example, distance, direction, speed, time, position, moving status, and the like).

In general, controller 380 processes data corresponding to proximity touches and proximity touch patterns sensed by the proximity sensor 341, and cause output of visual information on the touch screen. In addition, the controller 380 can control the mobile terminal 300 to execute different operations or process different data according to whether a touch with respect to a point on the touch screen is either a proximity touch or a contact touch.

A touch sensor can sense a touch applied to the touch screen, such as display unit 351, using any of a variety of touch methods. Examples of such touch methods include a resistive type, a capacitive type, an infrared type, and a magnetic field type, among others.

As one example, the touch sensor may be configured to convert changes of pressure applied to a specific part of the display unit 351, or convert capacitance occurring at a specific part of the display unit 351, into electric input signals. The touch sensor may also be configured to sense not only a touched position and a touched area, but also touch pressure and/or touch capacitance. A touch object is generally used to apply a touch input to the touch sensor. Examples of typical touch objects include a finger, a touch pen, a stylus pen, a pointer, or the like.

When a touch input is sensed by a touch sensor, corresponding signals may be transmitted to a touch controller. The touch controller may process the received signals, and then transmit corresponding data to the controller 380. Accordingly, the controller 180 may sense which region of the display unit 351 has been touched. Here, the touch controller may be a component separate from the controller 380, the controller 380, and combinations thereof.

In some embodiments, the controller 380 may execute the same or different controls according to a type of touch object that touches the touch screen or a touch key provided in addition to the touch screen. Whether to execute the same or different control according to the object which provides a touch input may be decided based on a current operating state of the mobile terminal 300 or a currently executed application program, for example.

The touch sensor and the proximity sensor may be implemented individually, or in combination, to sense various types of touches. Such touches includes a short (or tap) touch, a long touch, a multi-touch, a drag touch, a flick touch, a pinch-in touch, a pinch-out touch, a swipe touch, a hovering touch, and the like.

If desired, an ultrasonic sensor may be implemented to recognize position information relating to a touch object using ultrasonic waves. The controller 380, for example, may calculate a position of a wave generation source based on information sensed by an illumination sensor and a plurality of ultrasonic sensors. Since light is much faster than ultrasonic waves, the time for which the light reaches the optical sensor is much shorter than the time for which the ultrasonic wave reaches the ultrasonic sensor. The position of the wave generation source may be calculated using this fact. For instance, the position of the wave generation source may be calculated using the time difference from the time that the ultrasonic wave reaches the sensor based on the light as a reference signal.

The camera 321 typically includes at least one a camera sensor (CCD, CMOS etc.), a photo sensor (or image sensors), and a laser sensor.

Implementing the camera 321 with a laser sensor may allow detection of a touch of a physical object with respect to a 3D stereoscopic image. The photo sensor may be laminated on, or overlapped with, the display device. The photo sensor may be configured to scan movement of the physical object in proximity to the touch screen. In more detail, the photo sensor may include photo diodes and transistors at rows and columns to scan content received at the photo sensor using an electrical signal which changes according to the quantity of applied light. Namely, the photo sensor may calculate the coordinates of the physical object according to variation of light to thus obtain position information of the physical object.

The display unit 351 is generally configured to output information processed in the mobile terminal 100. For example, the display unit 351 may display execution screen information of an application program executing at the mobile terminal 300 or user interface (UI) and graphic user interface (GUI) information in response to the execution screen information.

In some embodiments, the display unit 351 may be implemented as a stereoscopic display unit for displaying stereoscopic images. A typical stereoscopic display unit may employ a stereoscopic display scheme such as a stereoscopic scheme (a glass scheme), an auto-stereoscopic scheme (glassless scheme), a projection scheme (holographic scheme), or the like.

The audio output module 352 is generally configured to output audio data. Such audio data may be obtained from any of a number of different sources, such that the audio data may be received from the wireless communication unit 310 or may have been stored in the memory 370. The audio data may be output during modes such as a signal reception mode, a call mode, a record mode, a voice recognition mode, a broadcast reception mode, and the like. The audio output module 352 can provide audible output related to a particular function (e.g., a call signal reception sound, a message reception sound, etc.) performed by the mobile terminal 300. The audio output module 352 may also be implemented as a receiver, a speaker, a buzzer, or the like.

A haptic module 353 can be configured to generate various tactile effects that a user feels, perceive, or otherwise experience. A typical example of a tactile effect generated by the haptic module 353 is vibration. The strength, pattern and the like of the vibration generated by the haptic module 353 can be controlled by user selection or setting by the controller. For example, the haptic module 353 may output different vibrations in a combining manner or a sequential manner.

Besides vibration, the haptic module 353 can generate various other tactile effects, including an effect by stimulation such as a pin arrangement vertically moving to contact skin, a spray force or suction force of air through a jet orifice or a suction opening, a touch to the skin, a contact of an electrode, electrostatic force, an effect by reproducing the sense of cold and warmth using an element that can absorb or generate heat, and the like.

The haptic module 353 can also be implemented to allow the user to feel a tactile effect through a muscle sensation such as the user's fingers or arm, as well as transferring the tactile effect through direct contact. Two or more haptic modules 353 may be provided according to the particular configuration of the mobile terminal 300.

An optical output module 354 can output a signal for indicating an event generation using light of a light source. Examples of events generated in the mobile terminal 300 may include message reception, call signal reception, a missed call, an alarm, a schedule notice, an email reception, information reception through an application, and the like.

A signal output by the optical output module 354 may be implemented in such a manner that the mobile terminal emits monochromatic light or light with a plurality of colors. The signal output may be terminated as the mobile terminal senses that a user has checked the generated event, for example.

The interface unit 360 serves as an interface for external devices to be connected with the mobile terminal 300. For example, the interface unit 360 can receive data transmitted from an external device, receive power to transfer to elements and components within the mobile terminal 300, or transmit internal data of the mobile terminal 300 to such external device. The interface unit 360 may include wired or wireless headset ports, external power supply ports, wired or wireless data ports, memory card ports, ports for connecting a device having an identification module, audio input/output (I/O) ports, video I/O ports, earphone ports, or the like.

The identification module may be a chip that stores various information for authenticating authority of using the mobile terminal 300 and may include a user identity module (UIM), a subscriber identity module (SIM), a universal subscriber identity module (USIM), and the like. In addition, the device having the identification module (also referred to herein as an "identifying device") may take the form of a smart card. Accordingly, the identifying device can be connected with the terminal 300 via the interface unit 360.

When the mobile terminal 300 is connected with an external cradle, the interface unit 360 can serve as a passage to allow power from the cradle to be supplied to the mobile terminal 300 or may serve as a passage to allow various command signals input by the user from the cradle to be transferred to the mobile terminal there through. Various command signals or power input from the cradle may operate as signals for recognizing that the mobile terminal is properly mounted on the cradle.

The memory 370 can store programs to support operations of the controller 380 and store input/output data (for example, phonebook, messages, still images, videos, etc.). The memory 370 may store data related to various patterns of vibrations and audio which are output in response to touch inputs on the touch screen.

The memory 370 may include one or more types of storage mediums including a Flash memory, a hard disk, a solid state disk, a silicon disk, a multimedia card micro type, a card-type memory (e.g., SD or DX memory, etc), a Random Access Memory (RAM), a Static Random Access Memory (SRAM), a Read-Only Memory (ROM), an Electrically Erasable Programmable Read-Only Memory (EEPROM), a Programmable Read-Only memory (PROM), a magnetic memory, a magnetic disk, an optical disk, and the like. The mobile terminal 300 may also be operated in relation to a network storage device that performs the storage function of the memory 170 over a network, such as the Internet.

The controller 380 may typically control the general operations of the mobile terminal 300. For example, the controller 380 may set or release a lock state for restricting a user from inputting a control command with respect to applications when a status of the mobile terminal meets a preset condition.

The controller 380 can also perform the controlling and processing associated with voice calls, data communications, video calls, and the like, or perform pattern recognition processing to recognize a handwriting input or a picture drawing input performed on the touch screen as characters or images, respectively. In addition, the controller 380 can control one or a combination of those components in order to implement various exemplary embodiments disclosed herein.

The power supply unit 390 receives external power or provide internal power and supply the appropriate power required for operating respective elements and components included in the mobile terminal 300. The power supply unit 390 may include a battery, which is typically rechargeable or be detachably coupled to the terminal body for charging.

The power supply unit 390 may include a connection port. The connection port may be configured as one example of the interface unit 360 to which an external charger for supplying power to recharge the battery is electrically connected.

As another example, the power supply unit 390 may be configured to recharge the battery in a wireless manner without use of the connection port. In this example, the power supply unit 390 can receive power, transferred from an external wireless power transmitter, using at least one of an inductive coupling method which is based on magnetic induction or a magnetic resonance coupling method which is based on electromagnetic resonance.

Various embodiments described herein may be implemented in a computer-readable medium, a machine-readable medium, or similar medium using, for example, software, hardware, or any combination thereof.

In accordance with still further embodiments, a mobile terminal may be configured as a device which is wearable on a human body. Such devices go beyond the usual technique of a user grasping the mobile terminal using their hand. Examples of the wearable device include a smart watch, a smart glass, a head mounted display (HMD), and the like.

A typical wearable device can exchange data with (or cooperate with) another mobile terminal 300. In such a device, the wearable device generally has functionality that is less than the cooperating mobile terminal. For instance, the short-range communication module 314 of a mobile terminal 300 may sense or recognize a wearable device that is near-enough to communicate with the mobile terminal. In addition, when the sensed wearable device is a device which is authenticated to communicate with the mobile terminal 300, the controller 380 may transmit data processed in the mobile terminal 300 to the wearable device via the short-range communication module 314, for example. Hence, a user of the wearable device can use the data processed in the mobile terminal 300 on the wearable device. For example, when a call is received in the mobile terminal 300, the user can answer the call using the wearable device. Also, when a message is received in the mobile terminal 300, the user can check the received message using the wearable device.

Figure 2:
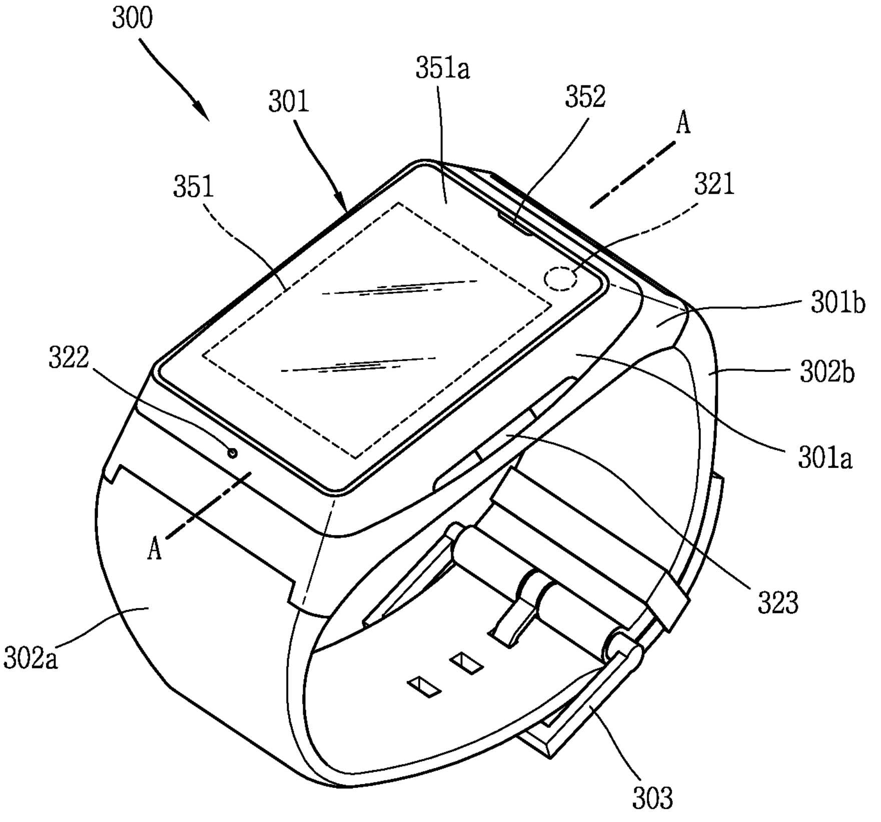
FIG. 2 is a perspective diagram illustrating one example of a watch-type terminal according to another embodiment of the present invention.

FIG. 2 is a perspective view illustrating one example of a watch-type mobile terminal 300 in accordance with another exemplary embodiment. As illustrated in FIG. 2, the watch-type mobile terminal 300 includes a main body 301 with a display unit 351 and a band connected to the main body 301 to be wearable on a wrist.

The main body 301 may include a case having a certain appearance. As illustrated, the case may include a first case 301*a* and a second case 301*b* cooperatively defining an inner space for accommodating various electronic components. Other configurations are possible. For instance, a single case may alternatively be implemented, with such a case being configured to define the inner space, thereby implementing a mobile terminal 300 with a uni-body.

The watch-type mobile terminal 300 can perform wireless communication, and an antenna 200 for the wireless communication (refer to FIG. 3A) can be installed in the main body 301.

The display unit 351 is shown located at the front side of the main body 301 so that displayed information is viewable to a user. In some embodiments, the display unit 351 includes a touch sensor so that the display unit can function as a touch screen. As illustrated, window 351*a* is positioned on the first case 301*a* to form a front surface of the terminal body together with the first case 301*a*.

The illustrated embodiment includes audio output module 352, a camera 321, a microphone 322, and a user input unit 323 positioned on the main body 301. When the display unit 351 is implemented as a touch screen, additional function keys may be minimized or eliminated. For example, when the touch screen is implemented, the user input unit 323 may be omitted.

The band is commonly worn on the user's wrist and may be made of a flexible material for facilitating wearing of the device. As one example, the band may be made of fur, rubber, silicon, synthetic resin, or the like. The band may also be configured to be detachable from the main body 301. Accordingly, the band may be replaceable with various types of bands according to a user's preference.

In one configuration, the band may be used for extending the performance of the antenna. For example, the band may include therein a ground extending portion (not shown) electrically connected to the antenna to extend a ground area.

The band may include fastener 303. The fastener 303 may be implemented into a buckle type, a snap-fit hook structure, a Velcro® type, or the like, and include a flexible section or material. The drawing illustrates an example that the fastener 303 is implemented using a buckle.

The band includes a first band 302*a* and a second band 302*b* extending from two ends of the main body 301 which face each other. End portions of the first band 302*a* and the second band 302*b* may be connected to each other by the fastener 303.

Figure 3A:
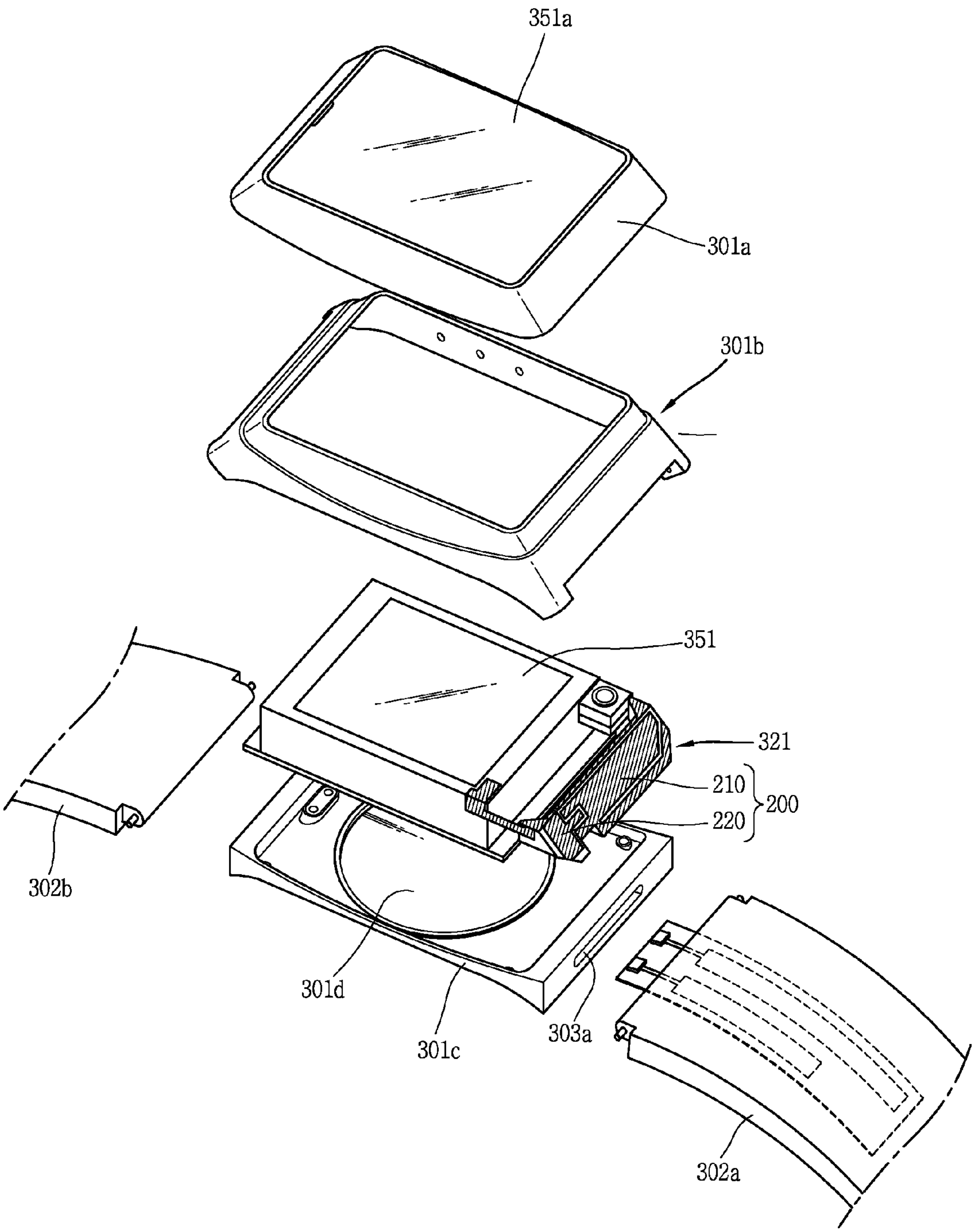
FIG. 3A is a perspective exploded diagram of the watch-type terminal in FIG. 2.
Figure 3B:
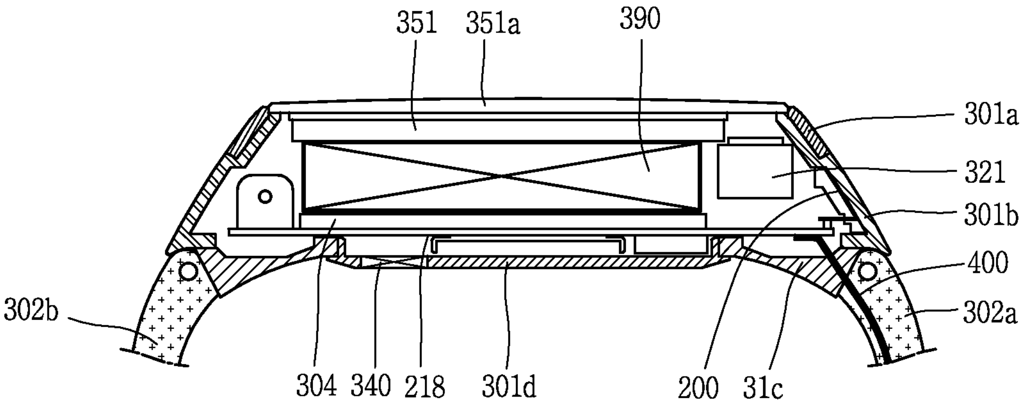
FIG. 3B is a cross-sectional diagram taken along a line A-A in FIG. 3.

FIG. 3A is a perspective exploded diagram of a watch-type terminal. FIG. 3B is a cross-sectional diagram taken along a line A-A in FIG. 2. Referring to FIGS. 3A and 3B, as cases that make up the main body 301 of the terminal, there are a case 301*a* that surrounds an edge of the window 351*a*, and second and third cases 301*b* and 301*c* that are sequentially attached to the bottom of the first case 301*a*.

The second case 301*b* has an accommodation space in the middle. Various components are mounted in the accommodation space. A nest space is formed in an upper end portion of the second case 301*b*. The first case 301*a* occupies the nest space and thus is nested.

The first case 301*a* is made of metal material that is wear resistant and scratch resistant. The second case 301*b* is made of dielectric material for improving radiation quality of the antenna 200. The third case 301*c* includes a cover 301*d* for inserting a SIM card that is attachable and detachable.

A sensing unit 340 is formed in a region adjacent to the cover 301*d*. The sensing unit 340 detects whether or not the watch-type terminal is worn.

For example, the sensing unit 340 is configured as a heartbeat sensor 344 that biological information (for example, a heart rate). When the watch-type terminal 300 is powered on, the controller 380 controls the heartbeat sensor 344 in such a manner that biological information on a user is detected at predetermined time the watch-type terminal 300. When the biological information is collected by the heartbeat sensor 344, the controller 380 recognizes that the watch type terminal 300 is in a worn state. When the biological information is not collected, the controller 180 recognizes that the watch type terminal 300 is in a non-worn state.

Alternatively, the sensing unit 340 is configured as a gap sensor that detects electrostatic capacitance. In a case where an object with electrostatic capacitance comes into contact with the cap sensor, the cap sensor detects a change in electric field formed between two electrodes. That is, in a case where the watch-type terminal 300 is worn on a wrist, it is desirable that the cap sensor is arranged in a region that comes into contact with a user's body. When the change in electric field is detected due to the contact with the user's body, the controller 380 determines that the watch-type terminal 300 is in the worn state.

The antenna 200 includes a first conductor 210 and a second conductor 220 that is arranged to be positioned a distance away from the first conductor 210 in such a manner that an electric coupling with the first conductor 210 occurs. However, the first and second conductors 210 and 220 are not limited to those illustrated in FIG. 3A.

The first conductor 210 is formed in such an arbitrary pattern that a length of the first conduction 210 is suitable for a resonance frequency band. The first conductor 210 is electrically connected to a circuit board 381 through an electric power supply unit (not illustrated). The second conductor 220 is formed in such a manner that the electric coupling with the first conduction occurs in order to increase a high-band bandwidth.

The first conductor 210 is formed in such a manner the first conductor 210 is resonated in low bands including GSM 800-band to GSM-900 band and the like, and in multiple bands including PCS-1600 to PCS-1900, W2100, and the like. The second conductor 220 is formed in such a manner that the second conductor 220 plays a role in causing the electric coupling to occur in a high band and thus increasing a bandwidth.

The second conductor 210 is connected to a ground portion 400 that is arranged in a band. The band includes a first band portion 302*a* and a second band portion 302*b*. The ground portion 400 according to one embodiment of the present invention includes multiple metal members that have different lengths. The antenna 200 is connected to at least one of the multiple metal members for grounding. A specific construction of the ground portion 400 will be described in detail below.

Figure 4A:
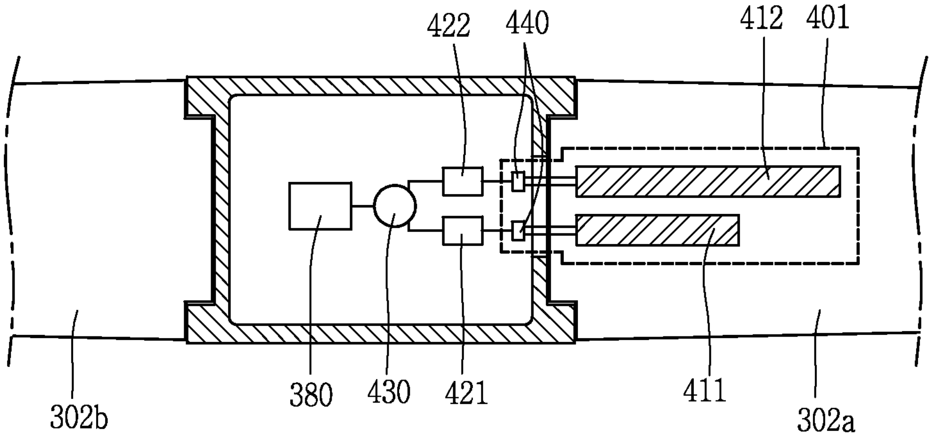
FIG. 4A is a diagram for describing a construction of a ground portion according to one embodiment of the present invention.
Figure 4B:
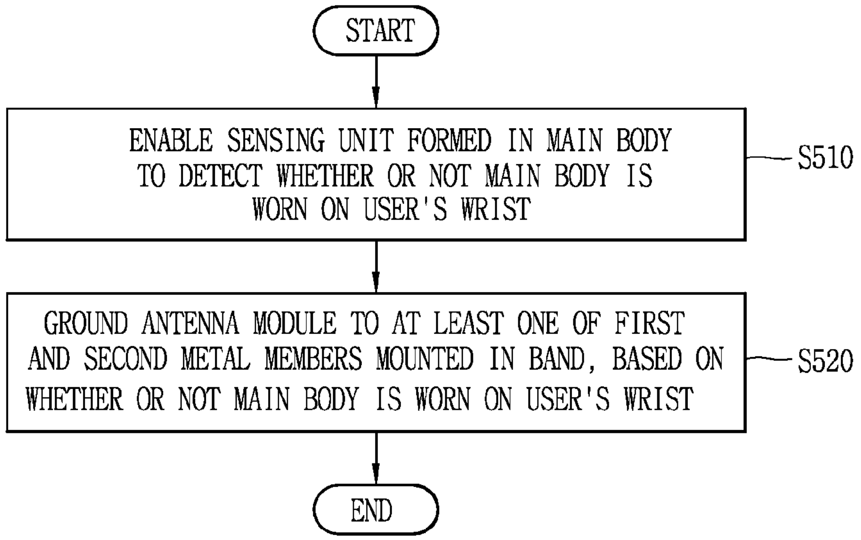
FIG. 4B is a flowchart for describing a control method of grounding an antenna according to one embodiment.

FIG. 4A is a diagram for describing the construction of the ground portion 400 according to one embodiment of the present invention. FIG. 4B is a flowchart for describing a control method of grounding the antenna according to one embodiment of the present invention. FIG. 4D is a graph illustrating a result of measuring performance of the antenna that varies with a length of the metal member with the antenna being grounded in the non-worn state.

The ground portion 400 according to the present embodiment is formed in the band, and includes first and second metal members 411 and 412 that have different lengths. The first and second metal members 411 and 412 extends in a direction in which the first band portion 302*a* extends. The first and second metal members 411 and 412 are formed to be positioned a distance away from each other. It is desirable that the first and second metal members 411 and 412 be arranged side by side along a direction perpendicular to the direction in which the first band portion 302*a* extends. That is, the first and second metal members 411 and 412 are arranged in parallel with each other within the first band portion 302*a*.

The first and second metal members 411 and 412 are in the form of a circuit board that is printed on an insulating film. For example, the first and second metal members 411 and 412 are realized as a flexible copper clad laminates (FCCL). However, the first and second metal members 411 and 412 are not limited to this. For example, the first and second metal members 411 and 412 may be realized as ones in the form of metal plates that have different lengths.

Alternatively, the first and second metal members 411 and 412 may be realized as ones in the form of flexible conductive tapes that are made of conductive material.

A flexible circuit board 401 protrudes from the first band portion 302*a* for connection to the main body 301. Specifically, the flexible circuit board 401 includes multiple terminals 440 that are connected to the first and second metal members 411 and 412, respectively. The multiple terminals 440 are electrically connected to first and second variable elements 421 and 422, respectively.

The first and second variable elements 421 and 422 are formed in such a manner that inductance values and capacitance values of the first and second variable elements 421 and 422 are changed within a predetermined range, respectively. The first and second variable elements 421 and 422 are realized as pin diodes. The inductance values and the capacitance values that are adjusted by the first and second variable elements 412 and 422 are set based on communication performance of the antenna 200 and lengths of the first and second metal members 411 and 412.

The first and second variable elements 412 and 422 are connected to a switch 430. The switch 430 is realized as a single pole double throw (SPDT) switch or a single pole 4 throw (SP4T) switch. However, the switch 430 is not limited to these, and is configured as any one of a semiconductor switch, such as a diode switch, a field effect transistor (FET) switch, a complementary metal oxide silicon (CMOS) switch, or a high electron mobility transistor (switch), and a micro electro mechanical system (MEMS) switch.

The switch 430 is controlled by a controller 380 in such a manner that at least one of the first and second metal members 411 and 412 is connected to the antenna 200.

The sensing unit 340 detects whether or not the main body 301 is worn on the user's wrist (S510). Bases on whether or not the main body 301 is worn on the user's wrist, the controller 380 grounds the antenna to at least one of the first and second metal members 411 and 412, which are mounted in the first band portion 302*a* (S520).

For example, in a case where the sensing unit 340 detects that the main body 301 is worn on the user's wrist, the controller 380 controls the switch 430 in such a manner that the antenna 200 is grounded to the second metal member 412. On the other hand, in a case where the sensing unit 340 detects that the main body 301 is removed from the user's wrist (that is, detects that the main body 301 is positioned a distance away from the user's body), the controller 380 control the switch 430 in such a manner that a connection to the second metal member 412 is released, the antenna 200 is connected to the first metal member 411, and thus the antenna 200 is grounded to the first metal member 411.

Referring to FIG. 4D, it is desirable that the first metal member 411 be approximately 70 mm in length in order for the antenna 200 to accomplish optimal wireless performance in a low band (ranging from approximately 700 MHz to proximately 900 MHz).

On the other hand, in a case where the sensing unit 340 detects that the main body 301 is worn on the user's wrist, the controller 380 controls the switch 430 in such a manner that the connection of the antenna 200 to the first metal member 411 is released and the antenna 200 is grounded to the second metal member 412. In this case, it is desirable that the second metal member 412 be approximately 20 mm in length.

Additionally, in a case where the first metal member 411 of the first and second metal members 411 and 412 stays connected to the antenna 200 and the main body 301 is separated from the user's wrist, the controller 380 controls the switch 340 in such a manner that the second metal member 412 is additionally connected to the antenna 200.

Figure 4C:
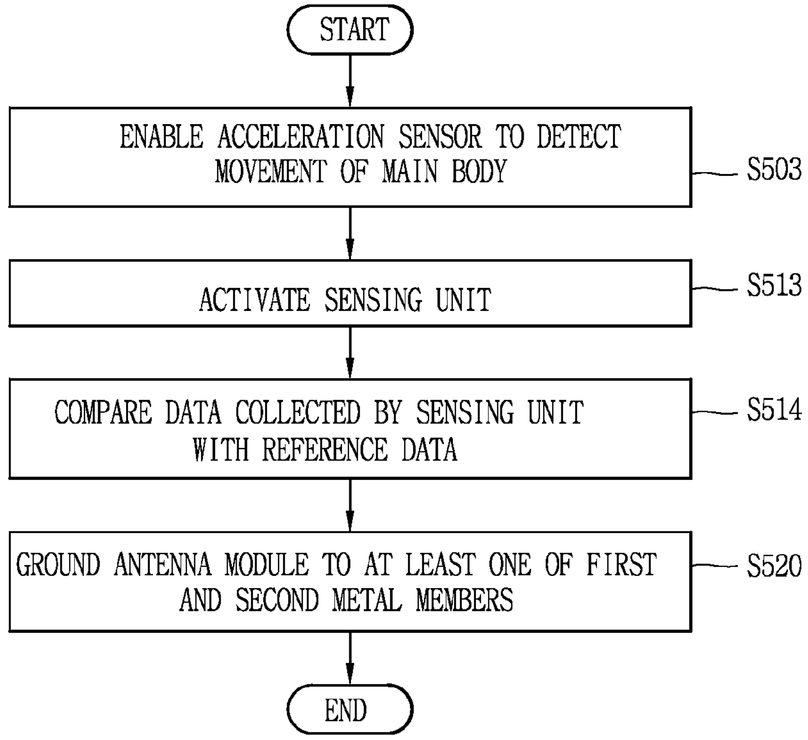
FIG. 4C is a flowchart for describing a method of controlling a watch-type terminal according to another embodiment.
Figure 4D:
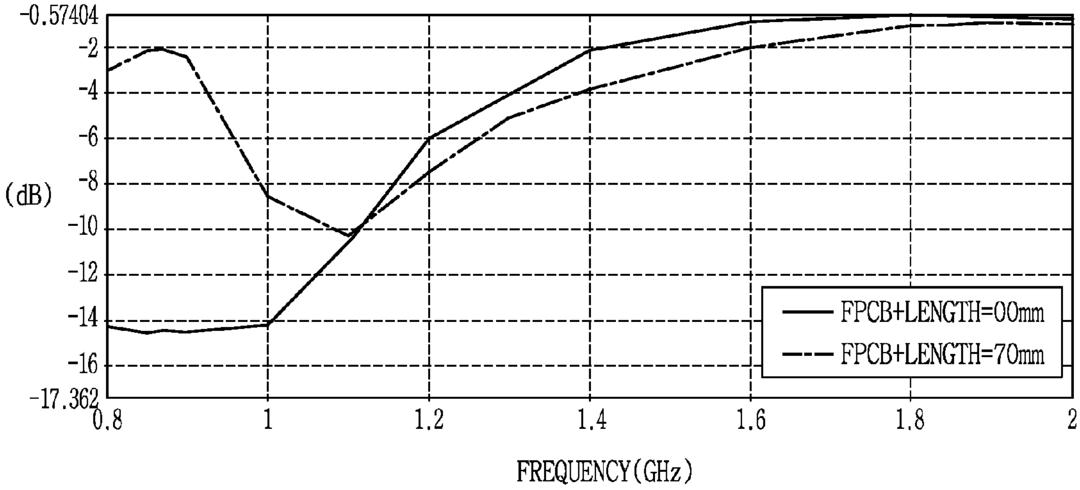
FIG. 4D is a graph illustrating a result of measuring performance of the antenna that varies with a length of a metal member with the antenna being grounded in a non-worn state.

FIG. 4C is a flowchart for describing a method of controlling a watch-type terminal according to another embodiment. The sensing unit 340 according to the present embodiment includes an acceleration sensor 343 that detects the movement of the main body 301, and a sensing module that collects the biological information on the user. For example, the sensing module corresponds to the heartbeat sensor 344 that detects a user's heart rate.

The controller 380 performs control in such a manner that the acceleration sensor 343 detects a movement of the main body 301 (S503). For example, the controller 380 activates the acceleration sensor 343 according to a predetermined period while the wireless communication network is performed. When the acceleration sensor 343 detects the movement of the main body 301, the controller 380 activates the sensing module (S513).

For example, when it is detected that the main body 301 is rapidly moved or is rapidly rotated, the controller 380 predicts that the use will wear or remove the watch-type terminal, and activates the sensing module in order to determine whether or not the watch-type terminal is worn.

The controller 380 compares data collected by the sensing module with pre-stored reference data (S514). For example, this is done when a change in the heart rate that is collected continues to be detected for a reference time or when a specific value of a dielective constant is detected.

Based on the data detected by the sensing module, the controller 380 determines whether the main body 301 is in the worn state or in the non-worn state. Depending on a result of the determination, the controller 380 grounds the antenna 200 to at least one of the first and second metal members 411 and 412.

According to the present invention, in a case where the main body into which the antenna 200 is built approaches the user's body, the antenna 200 is selectively grounded to the metal member that is shorter in length, thereby minimizing an influence that a change in the dielective constant due to an influence of the body takes on the wireless communication.

In addition, it is detected whether or not the watch-type terminal is worn on the user's body, and the grounding of the antenna is controlled depending on whether or not the watch-type terminal is worn on the user's body. Thus, there is no need for the user to perform a separate control step.

Figure 5:
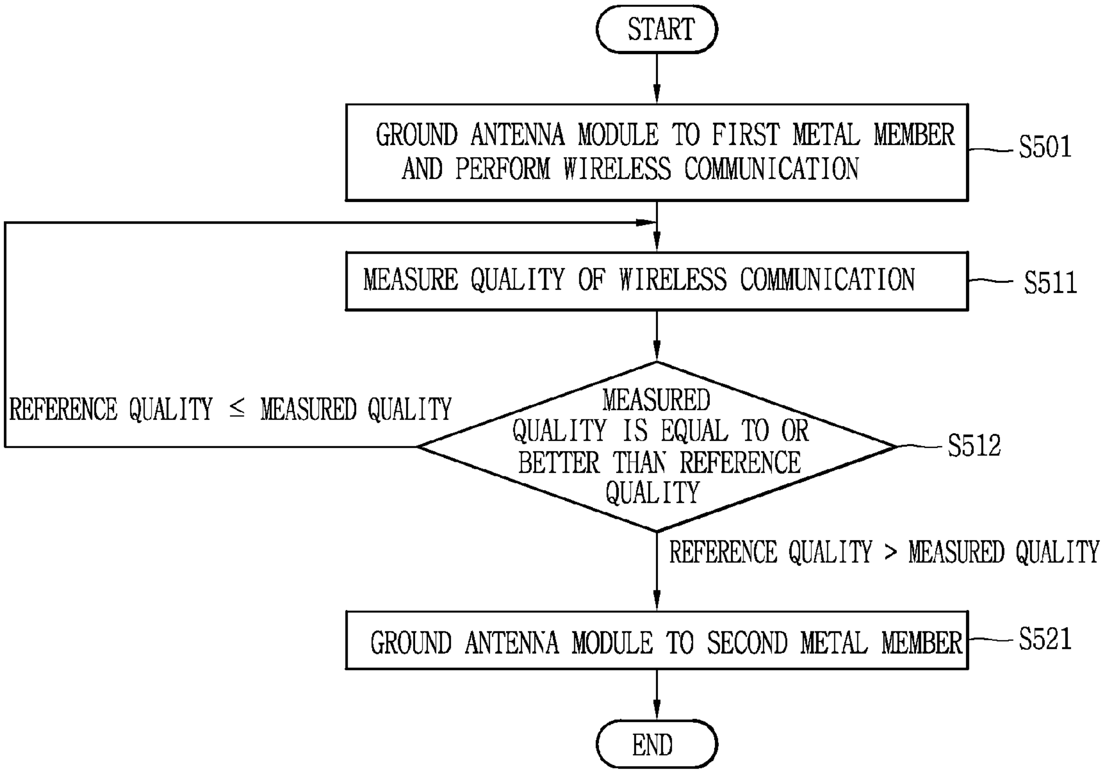
FIG. 5 is a flowchart for describing a control method of grounding the antenna according to another embodiment.

FIG. 5 is a flowchart for describing a control method of grounding the antenna according to another embodiment.

The controller 380 controls the switch 340 in such a manner that the antenna 200 is grounded to the first metal member 411, and controls the antenna 200 in such a manner that the wireless communication is performed (S501). For example, in a case where the watch-type terminal is powered on, a predetermined application is executed, the controller 380 activates the antenna 200.

When the antenna 200 is activated, the controller 380 controls the sensing unit 340 in such a manner that wireless communication quality of the antenna 200 is measured (S511). For example, the sensing unit 340 is configured as a communication measurement sensor 345 that detects the communication performance of the antenna 200. The communication measurement sensor 345 measures an Ec/Io ratio (a dimensionless ratio of the average power of some code distinguished CDMA signal channel, typically a pilot, to the total power comprised of signal plus interference, within the signal bandwidth), and a radio signal strength indicator (RSSI).

The controller 380 compares the measured quality with predetermined reference quality (S512). For example, by definition, the defined reference quality is when a value of Ec/Io is −90 dB and a value of the radio signal strength indicator is −90. In a case where the measured quality is equal to or better than the reference quality, the controller 380 maintains a state in which the antenna 200 is grounded to the first metal member 411. In addition, the controller 380 measures the communication performance and provides a comparison of the communication performance, with a predetermined period. At this point, the measured quality and the reference quality are determined by a comparison of the value of Ec/Io and the value of the RSSI.

On the other hand, in a case where the measured quality is poorer than the reference quality, the controller 380 grounds the antenna 200 to the second metal member 412.

For example, in a state where the antenna is grounded to the first metal member 411, when the main body 301 is positioned a distance away from the users body, the performance of the antenna is degraded. In this case, the communication measurement sensor 345 measures the quality of the communication performance, and the antenna 200 is controlled in such a manner that the antenna 200 is grounded to the second metal member 412. According to a length of the ground, the condition in which the antenna 200 radiates changes and the communication performance is improved.

According to the present embodiment, the metal member for grounding of the antenna is selectively connected based on communication quality of the antenna, without an additional sensing unit that detects whether or not the main body 301 is worn on the body.

Figure 6A:
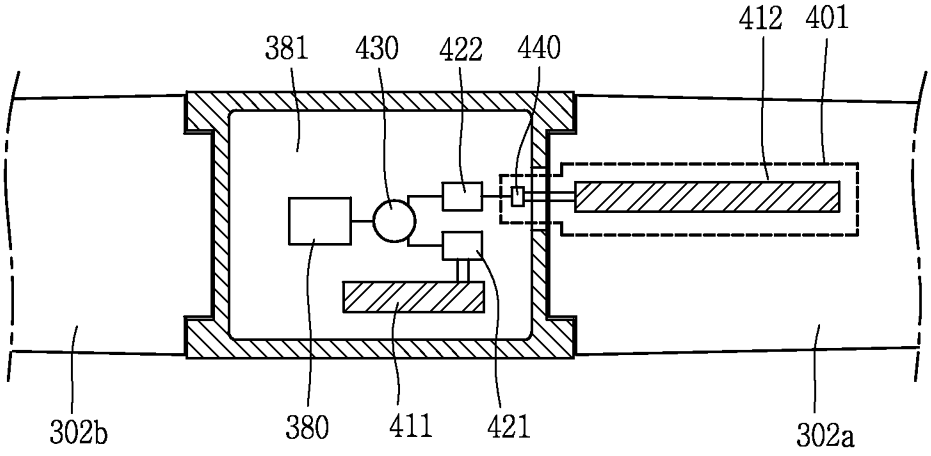
FIG. 6A is a diagram for describing a construction of a ground portion according to another embodiment.
Figure 6B:
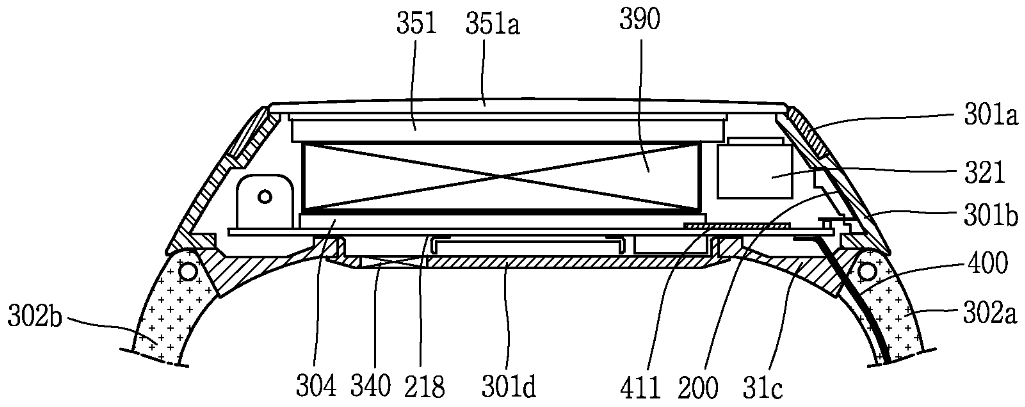
FIG. 6B is a cross-sectional diagram of the mobile terminal equipped with the ground portion in FIG. 6A according to the embodiment.

FIG. 6A is a diagram for describing a construction of a ground portion according to another embodiment. FIG. 6B is a cross-sectional diagram of the mobile terminal according to the embodiment in FIG. 6A. Constituent elements of the watch-type terminal in FIGS. 6A and 6B are substantially the same as those of the watch-type terminal in FIG. 4A except that the first metal member 411 is positioned differently in FIGS. 6A and 6B than in FIG. 4A. Therefore, constituent elements that are substantially the same as those in FIG. 4A are given the same reference numerals and descriptions of them are omitted.

Referring to FIG. 6A, the ground portion includes the first and second metal members 411 and 412, the first and second flexible elements 421 and 422, the terminal 330, and the switch 430. The second metal member 412 is arranged within the band, and is configured to be in the form of a circuit board.

The second metal member 412 is arranged in the main body 301. The terminal 440 and the switch 430 is arranged in the circuit board 381. The first metal member 411 is formed to be shorter than the second metal member 412, and is configured to be in the form of a metal that is printed on the circuit board 381. However, the first metal member 411 is not limited to this. The first metal member 411 is configured as a metal frame that makes up the main body 301, a case that makes up the external appearance of the watch-type terminal, or the like.

According to the present embodiment, a size of the metal member 412 formed in the first band portion 302*a* is minimized and thus a width of the band is minimized. Therefore, the band and the main body 301 can be connected to each other in a more stable manner.

Figure 7:
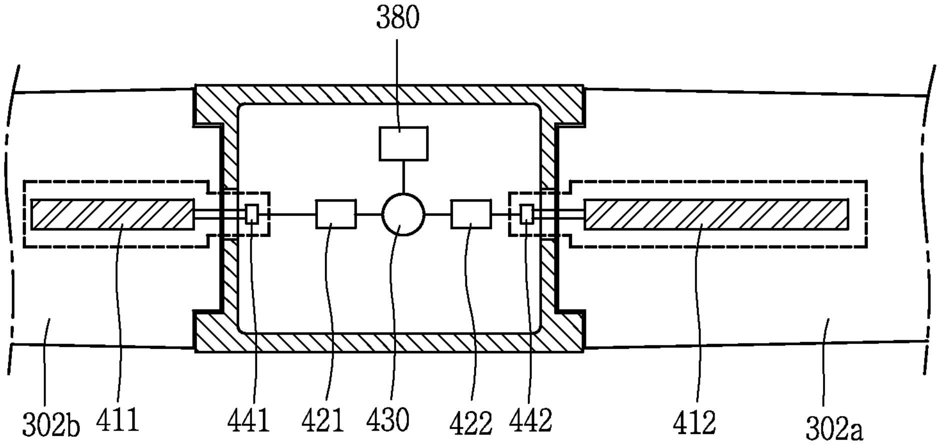
FIG. 7 is a diagram for describing a construction of a ground portion according to another embodiment.

FIG. 7 is a diagram for describing a construction of the ground portion according to another embodiment. Constituent elements of the watch-type terminal in FIG. 7 are substantially the same as those of the watch-type terminal in FIG. 4A except that the first metal member 411 is positioned differently in FIG. 7 than in FIG. 4A. Therefore, constituent elements that are substantially the same as those in FIG. 4A are given the same reference numerals and descriptions of them are omitted.

The first and second metal members 411 and 412 are arranged in the first and second band portions 302*a* and 302*b*, respectively. The first and second metal members 411 and 412 have different lengths and extend in directions which the first and second metal members 411 and 412 extend, respectively. The first and second metal members 411 and 412 are configured to be in the form of flexible circuit boards, and are electrically connected to the circuit board 381 by first and second terminals 441 and 442, respectively.

According to the present embodiment, the first and second metal members 411 and 412 extends are arranged in the first and second banda and 302*b* that extend in opposite directions, respectively. Thus, the first and second band portions 302*a* and 302*b* are formed that are substantially the same in width.

Figure 8A:
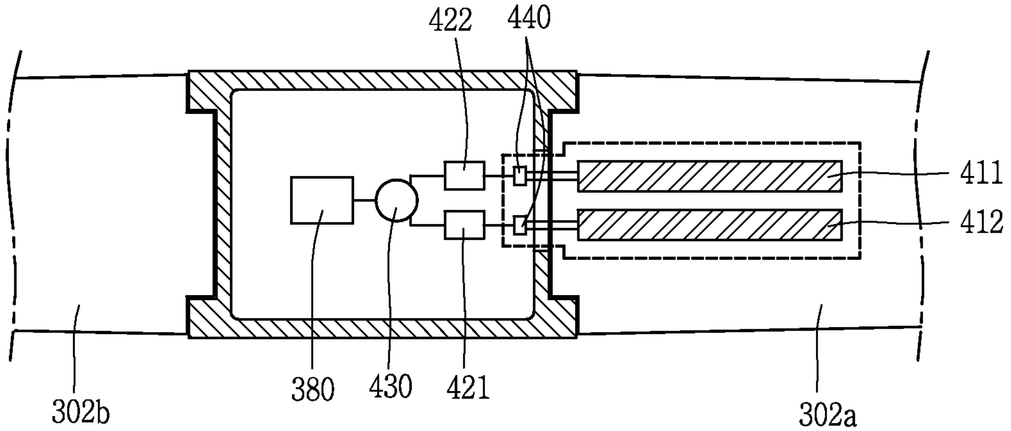
FIG. 8A is a diagram for describing a construction of a ground portion according to another embodiment.
Figure 8B:
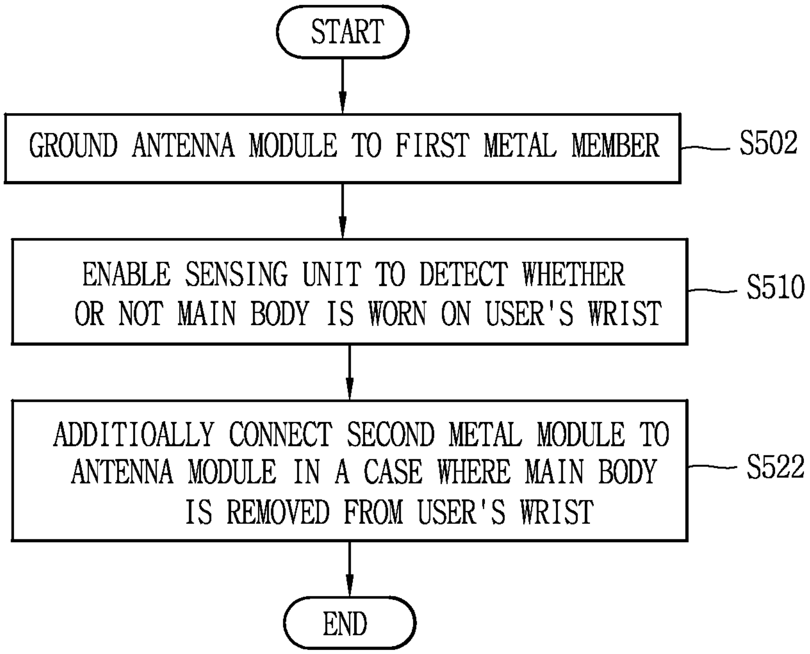
FIG. 8B is a flowchart for describing a method of controlling a watch-type terminal in FIG. 8A.

FIG. 8A is a diagram for describing a construction of the ground portion according to another embodiment. FIG. 8B is a flowchart for describing a method of controlling the watch-type terminal in FIG. 8A. Constituent elements of the watch-type terminal in FIG. 8A are substantially the same as those of the watch-type terminal in FIG. 4A except for lengths of the first and second metal members 411 and 412. Therefore, constituent elements that are substantially the same as those in FIG. 4A are given the same reference numerals and descriptions of them are omitted.

Referring to FIG. 8A, the first and second metal members 411 and 412 are formed to be substantially the same in length. The first and second metal members 411 and 412 are connected to the first and second flexible elements 421 and 422, respectively, and are set to be different in variable value from each other.

Referring to FIG. 8B, the antenna 200 is grounded to the first metal member 411 (S502). The sensing unit 340 detects whether or not the main body 301 is worn on the user's wrist (S510).

In a case where the main body 301 is separated from the user's wrist, the controller 380 controls the switch 430 in such a manner that the second metal member 412 is additionally connected to the antenna 200, and thus the antenna 200 is grounded to the first and second metal members 411 and 412 (S522).

That is, in the case where the main body 301 is separated from the user's wrist, the controller 380 additionally connects the metal member to the antenna, and thus extends a region of the ground portion. This satisfies a radiation condition in a specific frequency band.

According to another embodiment, the controller 380 activates the antenna 200 in a state where the antenna 200 is grounded to the first metal member 411. In addition, the controller 380 controls the sensing unit 340 in such a manner that the wireless communication quality of the antenna 200 is measured.

In this case, in a case where the wireless communication quality is poorer than the reference quality, the controller 380 additionally connects the second metal member 412 to the antenna 200.

However, a construction in which the first and second metal members 411 and 412 that have the same length are arranged is not limited to that illustrated in FIG. 8A.

Figure 9A:
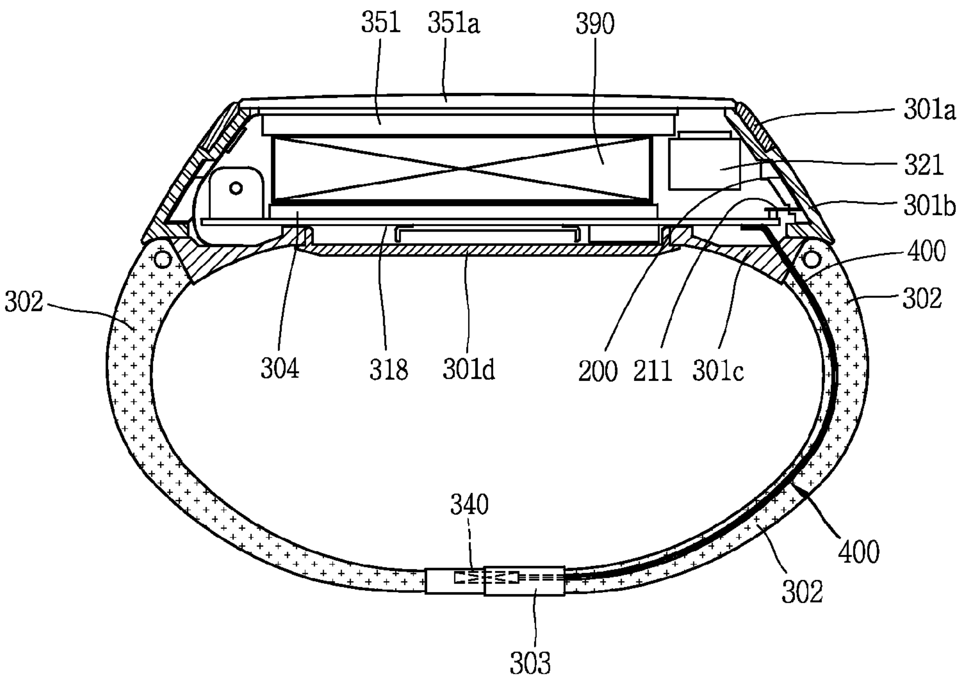
FIGS. 9A and 9B are diagrams for describing a ground portion of a watch-type terminal according to another embodiment.
Figure 9B:
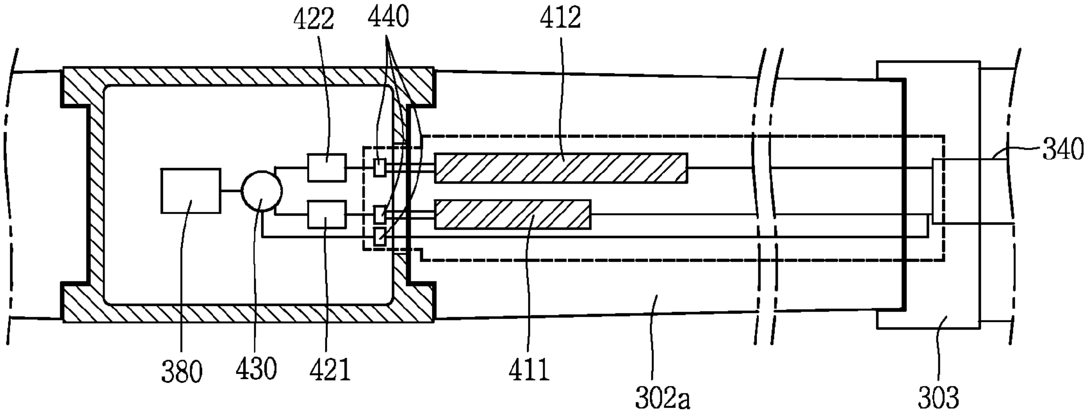

FIGS. 9A and 9B are diagrams for describing a ground portion of a watch-type terminal according to another embodiment. The sensing unit 340 of the watch-type terminal according to the present embodiment is formed in a fastener 303. Constituent elements of the watch-type terminal according to the present embodiment are substantially the same as those of the watch-type terminal in FIG. 4A except from a construction of the sensing unit 140. Therefore, constituent elements that are the same as those in FIG. 4A are given the same reference numerals and descriptions of them are omitted.

The sensing unit 340 detects whether or not the fastener 303 is connected. For example, the sensing unit 340 may be configured as a switch that generates a signal when the fastener 303 in the form of a buckle is connected and thus the switch is pushed. However, the sensing unit 140 that is formed in the fastener 303 is not limited to this, and may be configured as a sensor that detects whether the fastener 303 is fixed.

Although not specifically illustrated in the drawings, the sensing unit 340 may be configured to include a switch that is mounted on the fastener 303 and a sensor module that collects the biological information on the user. In this case, when the switch detects that the fastener 303 is fixed, the controller 380 performs control in such a manner that the sensor module is activated.

A circuit board, which extends from the main body 301 to the fastener 303, is formed in the first band portion 302*a*. The first and second metal members 411 and 412 are formed on the circuit board.

For example, when the sensing unit that is formed on the fastener 303 detects that the fastener 303 is fixed, the controller 380 controls the switch 430 in such a manner that the first metal member 411 is connected to the antenna 200.

According to the present embodiment, the sensing unit is formed in the fastener 303 and thus a space is secured within the main body 301.

Figure 10:
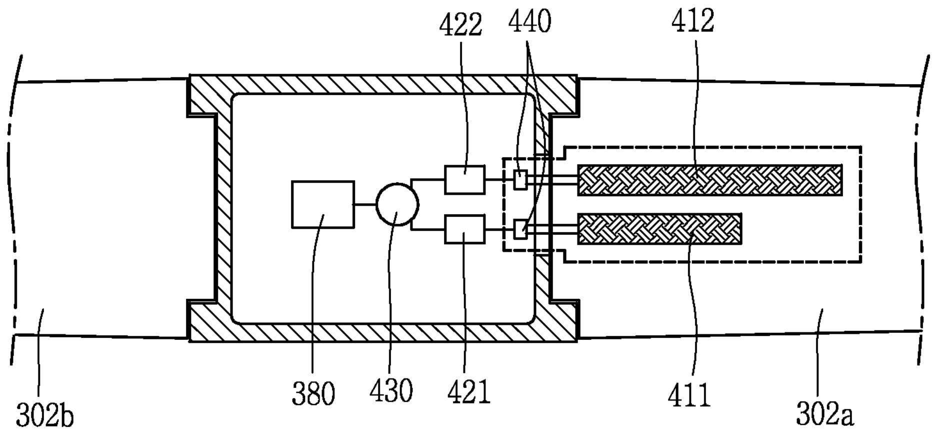
FIG. 10 is a diagram for describing a construction of a watch-type terminal according to another embodiment.

FIG. 10 is a diagram for describing a construction of a watch-type terminal according to another embodiment.

Referring to FIG. 10, the first and second metal members 411 and 412 are configured to be in the form of a mesh. That is, the first and second metal members 411 and 412 are printed in the form of a net. According to the present embodiment, the transformation and the wear of the metal member that is built into the band that is able to change in shape while in use are minimized.

Various embodiments may be implemented using a machine-readable medium having instructions stored thereon for execution by a processor to perform various methods presented herein. Examples of possible machine-readable mediums include HDD(Hard Disk Drive), SSD (Solid State Disk), SDD(Silicon Disk Drive), ROM, RAM, CD-ROM, a magnetic tape, a floppy disk, an optical data storage device, the other types of storage mediums presented herein, and combinations thereof. If desired, the machine-readable medium may be realized in the form of a carrier wave (for example, a transmission over the Internet). The processor may include the controller 180 of the mobile terminal.

The foregoing embodiments and advantages are merely exemplary and are not to be considered as limiting the present disclosure. The present teachings can be readily applied to other types of apparatuses. This description is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments.

As the present features may be embodied in several forms without departing from the characteristics thereof, it should also be understood that the above-described embodiments are not limited by any of the details of the foregoing description, unless otherwise specified, but rather should be considered broadly within its scope as defined in the appended claims, and therefore all changes and modifications that fall within the metes and bounds of the claims, or equivalents of such metes and bounds are therefore intended to be embraced by the appended claims.

What is claimed is:

1. A watch-type terminal comprising:

a main body that includes an antenna module configured to perform wireless communication in a defined frequency band;

a band coupled to the main body and being sized to be removably coupled to a user's wrist;

a ground portion that includes first and second metal members that extend to have respectively different lengths;

a sensor unit configured to sense biological information of a user when the main body is positioned at the user's body part;

a switch configured to selectively ground the antenna module; and a controller configured to:

determine that the main body is positioned at the user's body part when the sensor unit senses the biological information of the user;

determine that the main body is not positioned at the user's body part when no biological information is sensed by the sensor unit;

control the switch to ground the antenna module to the first metal member upon occurrence of the determining that the main body is not positioned at the user's body part; and control the switch to ground the antenna module to the second metal member upon occurrence of the determining that the main body is positioned at the user's body part.

2. The watch-type terminal of claim 1, wherein the sensor unit includes a heartbeat sensor that collects biological information for the user when the main body is positioned at the user's body part.

3. The watch-type terminal of claim 2, wherein the sensor unit includes an acceleration sensor that detects movement of the main body, and wherein the controller is further configured to:

activate the heartbeat sensor when the acceleration sensor detects the movement of the main body.

4. The watch-type terminal of claim 1, wherein the sensor unit includes a capacitance sensor that detects a change in capacitance that varies depending on whether the main body is positioned at the user's body part.

5. The watch-type terminal of claim 1, wherein the sensor unit is formed in such a manner that communication quality of the wireless communication is measured in a state where the watch-type terminal is activated.

6. The watch-type terminal of claim 5, wherein the controller is further configured to:

control the switch to ground the antenna module to the first metal member, and not the second metal member, when the communication quality of the wireless communication is below a reference quality; and control the switch to ground the antenna module to both the first metal member and the second metal member when the communication quality of the wireless communication meets or exceeds the reference quality.

7. The watch-type terminal of claim 6, wherein the quality of the wireless communication is determined by a value of Echo and a value of a radio signal strength indicator.

8. The watch-type terminal of claim 1, wherein the band coupled to the main body includes first and second band portions that are formed so that one end of the first band portion and one end of the second band portion are connected to opposite ends of the main body, and another end of the first band portion and another end of the second band portion are connected to each other, and wherein the first and second metal members are respectively mounted in the first and second band portions.

9. The watch-type terminal of claim 1, wherein the band coupled to the main body includes first and second band portions that are formed so that one end of the first band portion and one end of the second band portion are connected to opposite ends of the main body, and another end of the first band portion and another end of the second band portion are connected to each other, and wherein the first and second metal members are mounted in the first band portion.

10. The watch-type terminal of claim 9, wherein the first and second metal members extend in a direction in which the first band portion extends from the main body, and wherein the first and second metal members are arranged side by side.

11. The watch-type terminal of claim 1, wherein the first metal member is mounted in the main body, and wherein the second metal member is mounted in the band.

12. A method of controlling a watch-type terminal, comprising:

performing wireless communication using an antenna module that is coupled to a main body;

providing an output via a sensor unit to indicate whether the main body is positioned at a user's body part;

selectively ground the antenna module via a switch;

determining that the main body is positioned at the users body part when the sensor unit senses biological information of the user;

determining that the main body is not position at the users body part but no biological information is sent by the sensor unit;

controlling the switch to ground the antenna module to a first metal member upon occurrence over determining that the main body is not position at the users body part; and controlling the switch to ground the intent of module into a second mental member upon occurrence of determining that the main body is position at the users body part.

13. The method of claim 12, wherein the controlling the switch is further based on detected quality of the wireless communication.

14. The method of claim 12, wherein the sensor unit includes an acceleration sensor unit that detects movement of the main body, and wherein the method further comprises:

activating a heartbeat sensor unit when the acceleration sensor unit detects the movement of the main body.

15. A watch-type terminal comprising:

a main body that includes an antenna module configured to perform wireless communication in a defined frequency band;

a band coupled to the main body and being sized to be removably coupled to a user's wrist;

a ground portion that includes a first metal member that is mounted in the band, and extends to a predetermined length, and to which the antenna module is grounded, and a second metal members that has a same length as the first metal member;

a sensor unit configured to sense biological information of a user when the main body is positioned at the user's body part;

a switch configured to selectively ground the antenna module; and a controller configured to:

determine that the main body is positioned at the user's body part when the sensor unit senses the biological information of the user;

determine that the main body is not positioned at the user's body part when no biological information is sensed by the sensor unit;

control the switch to ground the antenna module to the first metal member upon occurrence of the determining that the main body is not positioned at the user's body part; and control the switch to ground the antenna module to the second metal member upon occurrence of the determining that the main body is positioned at the user's body part.

* * * * *